(12) United States Patent
Gavriely

(10) Patent No.: US 6,375,623 B1
(45) Date of Patent: Apr. 23, 2002

(54) DETERMINATION OF APNEA TYPE

(75) Inventor: Noam Gavriely, Haifa (IL)

(73) Assignee: Karmel Medical Acoustic Technologies Ltd., Yokneam-Illit (IL)

( * ) Notice: Subject to any disclaimer, the term of this patent is extended or adjusted under 35 U.S.C. 154(b) by 0 days.

(21) Appl. No.: 09/647,947

(22) PCT Filed: Mar. 30, 1999

(86) PCT No.: PCT/IL99/00188

§ 371 Date: Oct. 6, 2000

§ 102(e) Date: Oct. 6, 2000

(87) PCT Pub. No.: WO99/52438

PCT Pub. Date: Oct. 21, 1999

(30) Foreign Application Priority Data

Apr. 8, 1998 (WO) .............................. PCT/IL98/00173

(51) Int. Cl.[7] .......................... A61B 5/08; A61B 5/103; A61B 7/00

(52) U.S. Cl. ........................ 600/534; 600/529; 600/586; 600/595

(58) Field of Search ............................... 600/534, 535, 600/529, 595, 586

(56) References Cited

U.S. PATENT DOCUMENTS 4,306,567 A   12/1981  Krasner
5,309,922 A   5/1994   Schechter et al.
5,492,129 A   2/1996   Greenberger
5,671,733 A   9/1997   Raviv et al.
6,062,216 A * 5/2000   Corn .......................... 600/529
6,168,568 B1 * 1/2001  Gavriely ..................... 600/529
6,287,264 B1 * 9/2001  Hoffman ...................... 600/538

FOREIGN PATENT DOCUMENTS

WO   WO 98/14116   4/1998

OTHER PUBLICATIONS

Basano, L. et al; "A DSP Breath Sound Analyser"; Proceedings of the International Symposium on Circuits and Systems, ESPOO; vol. 3; No. conf. 21; pp. 2631–2634; Jun. 7, 1988.

Jingping, X. et al; "Spectrum Analysis of Lung Sounds"; Images of the Twenty First Century; vol. part 5; No. conf. 11; pp. 1676–1677; Nov. 9, 1989.

* cited by examiner

Primary Examiner—Kevin Shaver
Assistant Examiner—Navin Natnithithadha
(74) Attorney, Agent, or Firm—Fenster & Company Patent Attorneys, Ltd.

(57) ABSTRACT

A method of differentiating between OSA and CSA comprising: determining if chest motion above a chest motion threshold is present; determining if tracheal breath sound above a breath sounds threshold are present, classifying a state as OSA if the chest motion is above the threshold and the sounds are below the threshold; and classifying a state as CSA if both the chest motion and sounds are below their respective thresholds.

54 Claims, 3 Drawing Sheets

DETERMINATION OF APNEA TYPE

RELATED APPLICATIONS

The present application is a US national application of PCT/IL99/00188, filed Mar. 30, 1999.

FIELD OF THE INVENTION

The present invention relates to the field of determination of breathing disorders and more particularly to the determination of Apnea and Hypopnea and in particular of the type of Apnea.

BACKGROUND OF THE INVENTION

Apnea is defined as cessation of breathing activity for a certain duration (6–20 seconds). Hypopnea is either slow breathing or shallow breathing or both. Detection of apnea/hypopnea (AH) is important in the diagnosis of the sleep apnea syndrome (SAS), a condition that afflicts 2% of adult females and 4% of adult male population in western countries. Detection of AH is also important in the diagnosis of breathing irregularity conditions in children and elderly patients. The diagnosis of SAS is traditionally performed in a sleep lab, but in recent years devices for home analysis of performance have been developed to offset the substantial cost and inconvenience of a full sleep lab study.

Detection of AH in a sleeping subject requires identification of actual air flow into and out of the thorax. Thus, mere monitoring of chest motion as performed with impedance pneumography is not sufficient. The existing technology is based on the use of thermal sensors in the nostrils and/or the use of chest and abdomen volume monitors (for example, inductive plethysmography which is available under the trade name Respitrace™. These methods either require instrumentation of the patient's face or use of circumferential belts around the chest and abdomen. Both approaches impose substantial inconvenience and are prone to data corruption.

One aspect of apnea detection is the prevention of sudden infant death syndrome (SIDS), the leading cause of death in infants 1–12 months old in western societies. While the etiology of SIDS is obscure, it is broadly believed that if the cessation of breathing is detected in time and resuscitate measures are taken the baby can be saved. Based on this notion many monitoring devices for home use have been introduced into the market. Unfortunately, the technology of many such devices results in many false alarms being activated, often wearing the mental stability of the parents to the point where use of the device is discontinued.

Most of the existing devices rely on monitoring the electrical impedance of the chest However, the chest impedance shows continued substantial oscillations when the breath is held due to the action of the heart within the chest. To prevent this cardiac activity from being detected as breathing activity, the detection algorithm parameters and threshold must be set such that false detection of apnea is almost inevitable. In practice, chest impedance measurements appear to be incapable of providing a clear indication of apnea without at the same time causing an undesirably high number of false alarms.

In PCT application PCT/IL97/00318, filed Sep. 30, 1997 and published as WO 98/144116 on Apr. 9, 1998, the disclosure of which is incorporated herein by reference, the present inventor described a breath sounds analysis system which includes a methodology for the detection of breath sounds in which at least one breath related sensor is placed around the respiratory system of a patient for measuring breath sound data signals; a breath analyzer which continuously matches the breath sound data signals produced by the at least one breath related sensor to at least a regular breath sound template to determine the presence of breathing and which provides an alert indication when no breathing is present for a time period longer than a given period.

In addition, the PCT application describes a method of determining the state of breathing of a patient, the method comprising determining the inspiration/expiration phase of a breath from chest movement data and defining a breath phase variable therefrom; if the tracheal breath sound data are significant and if the external noise is low determining if the tracheal breath sound data has a generally normal shape; and if not determining if the lack of flow indicates the presence of apnea and, if so, setting an apnea alarm. Preferably, the method includes generating a loud noise indication if the breath shape is not normal.

In a preferred embodiment of the invention described in the PCT application, the amplitude of the level of breath sounds are compared with an adaptive breath sounds threshold during consecutive periods of time. If the sound level is below a given level or if the detected sound does not match the spectral characteristic of authentic tracheal breath sounds, for a number of consecutive time periods an alarm may be sounded.

In preferred embodiments of the invention described in the PCT application, the breath sounds are identified as authentic breath sounds by matching the spectrum of the sounds to a spectrum which is determined during a reference period and/or by determining whether the spectral shape of the sounds, as characterized by certain parameters, is normal.

SUMMARY OF THE INVENTION

One aspect of the present invention presents an improved method and apparatus for the determination of apnea and hypopnea.

In a preferred embodiment of a method of the present invention, spectral power is used to determine the presence or absence of breath sounds. In a preferred embodiment of the invention, the average or integral of the sound power amplitude over a particular frequency range is used as a measure of the total breath flow. If the measure is below a threshold, an hypopnea alarm is preferably activated. If the measure is below a second, lower value, an apnea alarm is preferably activated.

In accordance with a further aspect of the invention, a running time average of the spectral power is used in the determination of apnea and/or hypopnea. The averaging time is made relatively short when it is desired to test for apnea in SIDS and relatively longer when sleep testing of adults is performed.

A third aspect of the invention is related to the measurement of breath sounds in the presence of noise. In the above referenced PCT application, an ambient sound sensor was used in order to determine the level of ambient sound. If the level of sound was too high, then no measurements were taken. In critical testing, such as SIDS testing, it is important to continue the testing even in the presence of some noise, as might be present in a household, such as a television in an adjoining room or the like.

In a preferred embodiment of the invention, the ambient sound is treated in the same manner as the breath sound. For frequencies at which the ambient sound level is higher than a certain level, the breath sound spectrum at that frequency is ignored in determining the breath sound power and flow. If the power of the ambient sound is above the certain level for too great a portion of the relevant spectrum, the measurement of breath power is aborted and an ambient noise indication is activated.

A fourth aspect of the invention involves the differentiation between Obstructive Sleep Apnea (OSA) and Central Sleep Apnea (CSA). While both these conditions involve cessation of breathing, with potentially lethal implications, the treatment for the two conditions is different. In particular, OSA is generally treated surgically or by a pressure device that overcomes the obstruction and CSA is not helped by either of these therapies and generally requires a neurological evaluation to determine treatment.

In accordance with a preferred embodiment of the invention, the two conditions are differentiated by determining if there is chest motion (expansion and contraction). When there is expansion and contraction of the chest, but no tracheal breath sounds, this absence of sound is presumed to be caused by an obstruction and the Apnea is classified as of the OSA type. If there are neither breathing movements nor sound, then the apnea is presumed to be centrally caused and the apnea is presumed to be of the CSA type.

There is thus provided, in accordance with a preferred embodiment of the invention a method of differentiating between OSA and CSA comprising:

determining if chest motion above a chest motion threshold is present;

determining if tracheal breath sound above a breath sounds threshold are present;

classifying a state as OSA if the chest motion is above the threshold and the sounds are below the threshold; and classifying a state as CSA if both the chest motion and sounds are below their respective thresholds.

Preferably, determining is performed on time segments of the chest motion and breath sounds.

Preferably, the chest motion threshold is determined based on a percentage of motion during normal breathing. Preferably, the chest motion threshold is between about 5% and about 10%. Preferably, the chest motion threshold is about 10% of a normal breathing chest motion.

In a preferred embodiment of the invention, the normal breathing is normal breathing during sleep.

In a preferred embodiment of the invention, determining whether tracheal breath sounds are present includes:

producing a spectrum of the breath sound signal;

summing averaging the spectrum over a given frequency range to produce a breath sounds power signal.

Preferably, the method includes producing a separate breath sound spectrum for each of a plurality of given time periods.

In a preferred embodiment of the invention, the method includes:

producing a breath sounds power signal representative of the breath sounds power in a plurality of given time periods; and integration circuitry which receives the breath sounds power signal; and producing a running time average or integral of the breath sounds power signal over a second given time period.

There is further provided, in accordance with a preferred embodiment of the invention, breath sounds apparatus for classifying a breathing state comprising:

a chest motion sensor and produces a chest motion signal;

a tracheal breath sound sensor that produces a breath sound signal;

computing circuitry that receives the breath sound signal and the chest motion signal and determines if chest motion above a chest motion threshold is present and if tracheal breath sound above a breath sounds threshold is present and classifies a breathing state as OSA if the chest motion is above the threshold and the sounds are below the threshold and classifies a breathing state as CSA if both the chest motion and sounds are below their respective thresholds.

In a preferred embodiment of the invention, the computing circuitry includes:

spectrum producing circuitry which receives the breath sound signal and produces a spectrum of the breath sound signal; and averaging circuitry which receives the spectrum and sums or averages the spectrum over a given frequency range to produce a breath sounds power signal, wherein the breath sounds power signal is used in the determination of whether the breath sounds are above their threshold.

There is further provided, in accordance with a preferred embodiment of the invention, apparatus for the detection of breathing activity, comprising:

a breath sound sensor which produces a breath sound signal responsive to breath sounds of a subject;

spectrum producing circuitry which receives the breath sound signal and produces a spectrum of the breath sound signal;

averaging circuitry which receives the spectrum and sums or averages the spectrum over a given frequency range to produce a breath sounds power signal.

In preferred embodiments of the invention the given frequency range has a lower frequency limit of at least 200 Hz, 250 Hz, 300 Hz or 400 Hz. In preferred embodiments of the invention the given frequency range has an upper frequency limit of 1200 Hz or less, 1300 Hz or less, 1400 Hz or less, 1500 Hz or less, 1800 Hz or less or 2000 Hz or less.

In a preferred embodiment of the invention the spectrum producing circuitry produces a separate breath sound spectrum for each of a plurality of given time periods.

There is further provided, in accordance with a preferred embodiment of the invention, apparatus for the classification of breathing activity, comprising:

a breath sensor which produces a breath sound signal responsive to breath sounds of a subject;

breath sounds power circuitry which receives the breath sounds signal and produces a breath sounds power signal representative of the breath sounds power in a plurality of given time periods; and integration circuitry which receives the breath sounds power signal and produces a running time average or integral of the breath sounds power signal over a second given time period.

Preferably, the breath sounds power circuitry comprises:

spectrum producing circuitry which receives the breath sound signal and produces a spectrum of the breath sound signal; and averaging circuitry which receives the spectrum and sums or averages the spectrum over a given frequency range to produce the breath sounds power signal.

In preferred embodiments of the invention the given time period is greater than 20, 50 or 75 msec. In preferred embodiments of the invention, the given time period is shorter than 200, 150, 100, 75 or 50 msec.

In accordance with a preferred embodiment of the invention, the apparatus includes integration circuitry which receives the breath sounds power signal and produces a running time average or integral of the breath sounds power signal over a second given time period.

In preferred embodiments of the invention the second given time period is at least 5 seconds, about 6 seconds, about 8 seconds, about 10 seconds, between about 10–15 seconds or between about 15–20 seconds.

Preferably, the apparatus includes comparison circuitry which receives the averaged or integrated breath sounds power signal and produces an apnea indication if the averaged breath sounds power signal is below a given apnea threshold. Preferably the given apnea threshold is based on a breath sounds power signal acquired during normal breathing. Preferably, the given apnea threshold is about 10% of the a breath sounds power signal acquired during normal breathing. Preferably, the given apnea threshold is between 5% and 10% of the a breath sounds power signal acquired during normal breathing.

Preferably the apparatus includes comparison circuitry which receives the averaged or integrated breath sounds power signal and produces an hypopnea indication if the averaged breath sounds power signal is below a given hypopnea threshold. Preferably, the given hypopnea threshold is based on a breath sounds power signal acquired during normal breathing. Preferably the given hypopnea threshold is about 25% of the a breath sounds power signal acquired during normal breathing. Preferably, the given apnea threshold is between 20% and 30% of the a breath sounds power signal acquired during, normal breathing.

In a preferred embodiment of the invention, the apparatus includes:

an ambient sound sensor which produces an ambient sound signal responsive to ambient sounds;

spectrum producing circuitry which receives the ambient sound signal and produces a spectrum of the ambient sound signal;

comparison circuitry which compares the spectrum of the ambient sound spectrum with a threshold spectrum and produces a signal for those frequencies for which the spectrum is greater than the threshold; and spectrum conditioning circuitry which conditions the breath sound spectrum by replacing the value of the breaths sounds spectrum by a different value for those frequencies for which the ambient sound spectrum exceeds the threshold.

There is further provided, in accordance with a preferred embodiment of the invention, apparatus for conditioning a breath sound signal to reduce the effects of ambient sound, comprising:

a breath sound sensor which produces a breath sound signal responsive to breath sounds of a subject;

spectrum producing circuitry which receives the breath sound signal and produces a spectrum of the breath sound signal;

an ambient sound sensor which produces an ambient sound signal responsive to ambient sounds;

spectrum producing circuitry which receives the ambient sound signal and produces a spectrum of the ambient sound signal;

comparison circuitry which compares the spectrum of the ambient sound spectrum with a threshold spectrum and produces a signal for those frequencies for which the spectrum is greater than the threshold; and spectrum conditioning circuitry which conditions the breath sound spectrum by replacing the value of the breaths sounds spectrum by a different value for those frequencies for which the ambient sound spectrum exceeds the threshold.

Preferably the threshold is based on an ambient sounds spectrum produced in the absence of substantial ambient sound. Preferably, the threshold at a given frequency is determined, from a plurality of spectra of the ambient sound, as the average of value of the spectrum at the given frequency plus a factor times the standard deviation of the values of the spectrum. Preferably, the factor is more than 3 or between 4 and 6.

In a preferred embodiment of the invention the spectrum conditioning circuit replaces the value of the breaths sounds spectrum by a zero for those frequencies for which the ambient sound spectrum exceeds the threshold. Alternatively, the spectrum conditioning circuit replaces the value of the breaths sounds spectrum by a value equal to the average of values for adjacent frequencies, for those frequencies for which the ambient sound spectrum exceeds the threshold.

There is further provided, in accordance with a preferred embodiment of the invention, a method differentiating between OSA and CSA comprising:

determining if chest motion above a chest motion threshold is present;

determining if tracheal breath sound above a breath sounds threshold are present;

classifying a state as OSA if the chest motion is above the threshold and the sounds are below the threshold; and classifying a state as CSA if both the chest motion and sounds are below their respective thresholds.

BRIEF DESCRIPTION OF THE DRAWINGS

The invention will be better understood form the following description of preferred embodiments thereof read in conjunction with the attached drawings in which.

DESCRIPTION OF PREFERRED EMBODIMENTS OF THE INVENTION

Figure 1A:
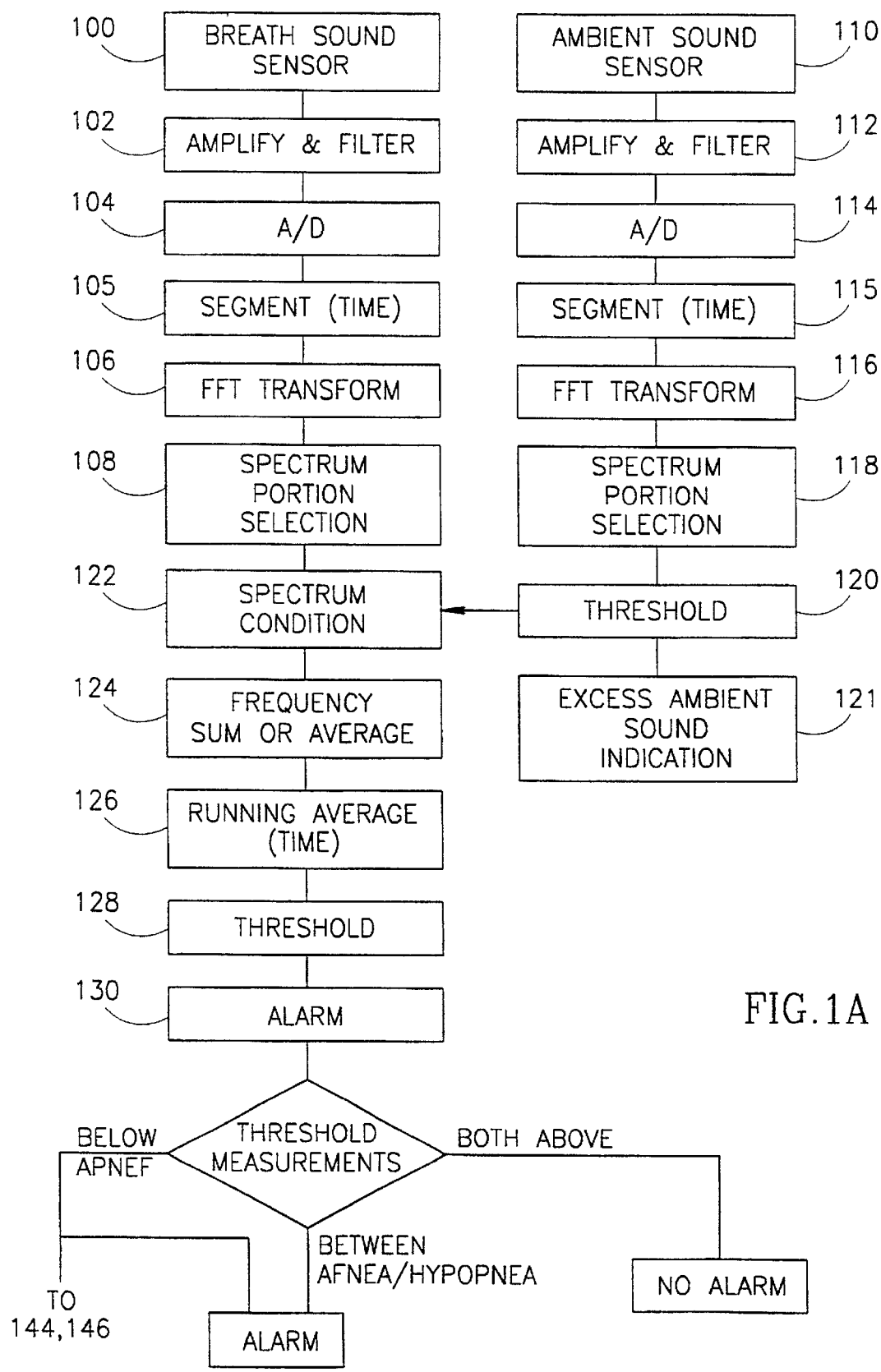
FIG. 1A is a simplified block diagram of a method of determining the presence of apnea and/or hypopnea, in accordance with a preferred embodiment of the invention.

Reference is made to FIG. 1A which is a block diagram of a method of determining the presence of apnea and/or hypopnea, in accordance with a preferred embodiment of the invention.

A tracheal breath sound sensor, placed for example on the anterior neck, over the sternal notch and/or over the anterior chest picks up a tracheal sound signal (at 100). This signal is preferably amplified and filtered (at 102). It has been found that a suitable filter is a 75–4000 Hz band pass filter, although other ranges may be used. The filtered signal is digitized using an A/D converter (at 104). It has been found that a 12 bit A/D is suitable, however, an A/D having a resolution between 8 bits and 16 bits may also be used. It has been found that a sampling rate of 8,000–15,000 samples/second, most preferably 11,025 samples/second, is suitable for the present invention. However, the a higher or lower rate is also suitable. The digitized signal is time segmented into time segments having a period of between preferably 20–100 msec, with about 50 msec being preferred (at 105) prior to further processing which is performed separately on each time segment. A digital FFT transformation is applied to each segment of the digitized signal (at 106) and a portion (or portions) of the resulting spectrum is selected (at spectrum portion selector 108) for measuring the power.

In a preferred embodiment of the invention, the spectrum portion selector selects the portion of the spectrum between about 200–1200 Hz. This effectively removes cardiac sounds from the signal and leaves those frequencies which are most characteristic of breath sounds. For children, a higher low frequency boundary is preferably used (for example, 250 Hz), since the cardiac sounds have higher frequencies in children. In other preferred embodiments of the invention selection having an upper frequency of 1300, 1400, 1500, 1800 or 2000 Hz may be used. The lower frequency should be sufficiently high to block out cardiac sounds. Thus in addition to the preferred low end of the range of selection frequencies of 200 and 250 Hz, low boundary frequencies of 300, 350, 400 or even higher may be used in some preferred embodiments of the invention.

It should be noted that while, in preferred embodiments of the invention, only the initial band pass filtering is carried out on the analog signal and the remaining processing is carried out digitally. However, it is possible to perform all of the processing on a digitized signal (with a higher sampling rate to avoid aliasing) or to perform more of the processing on the analog signal.

An ambient sounds sensor detects ambient sounds and a resulting signal is subjected to the same processing as the breath sounds signal (at 110, 112, 114, 115, 116 and 118). Each element of the resulting ambient spectrum is compared to a threshold spectrum (at 120) and if the spectrum at any frequency is greater than the threshold, the breath sound spectrum value is set to zero for that frequency or frequencies (at 122). Alternatively, a value equal to the average of the adjacent two or four frequencies is substituted for the value at that frequency. Preferably, if an excessive proportion of the ambient sound spectrum is above the threshold, an indication of excess ambient sound (at 121), such as an alarm, results. It will be noted that digital filter 118 is optional, since the resulting processing of the breath sounds spectrum is operative only for the frequencies in the band.

The conditioned breath spectrum is now preferably summed (at 124) to give the integrated energy of the breath sounds spectrum in the frequency range of 200–1200 Hz. More preferably this integrated energy is divided by the number of frequencies utilized in the summation to reduce the effect of spectrum lines which are blanked due to a high threshold of ambient sound at that frequency.

The sum or average (result of 124) which is a single number characteristic of the sound level of the breath sounds at the time of the segment is then averaged over time to give a value of the total average breathing activity (at 126). This running average may be an average over a period of between 5–20 seconds, depending on what is being monitored, with shorter times being used for neo-natal apnea (SIDS) and the longer times being used for a more general diagnostic survey of apnea and hypopnea in adults. If the time averaged signal falls below a first threshold a determination of hypopnea is made; if it falls below a second, lower, threshold, an indication of apnea is made (at 130).

In the determination of apnea and hypopnea described above, threshold values are utilized for measurements of the spectral lines of the ambient sound and for the determination of apnea and hypopnea. These thresholds are found in the following manner.

During a rest period in which ambient noise is suppressed (or non-existent) 110–118 are carried out over a period of several seconds. The 100 or so spectra which are the result of 118 over the period are averaged and a value equal to the average plus several times (four or five appears to work well) the standard deviation of the values for each of the spectral frequencies is used for the threshold of 120 for that frequency. Similarly, during this period, steps 108–126 are carried out to give a baseline value of breath sound strength. In a preferred embodiment of the invention, the threshold of 128 is set at 25% of this baseline for hypopnea and 10% of the baseline for apnea. It should be understood that these numbers are somewhat arbitrary, but are good practical values which correspond to results of conventional sleep lab studies.

In a further preferred embodiment of the invention, discrimination is made between Obstructive Sleep Apnea (OSA) and Central Sleep Apnea (CSA). In accordance with a preferred embodiment of the invention, the two conditions are differentiated by determining if there is chest motion (expansion and contraction). When there is expansion and contraction of the chest, but no tracheal breath sounds, this absence of sound is presumed to be caused by an obstruction and the Apnea is classified as of the OSA type. If there are neither breathing movements nor sound, then the apnea is presumed to be centrally caused and the apnea is presumed to be of the CSA type.

Figure 1B:
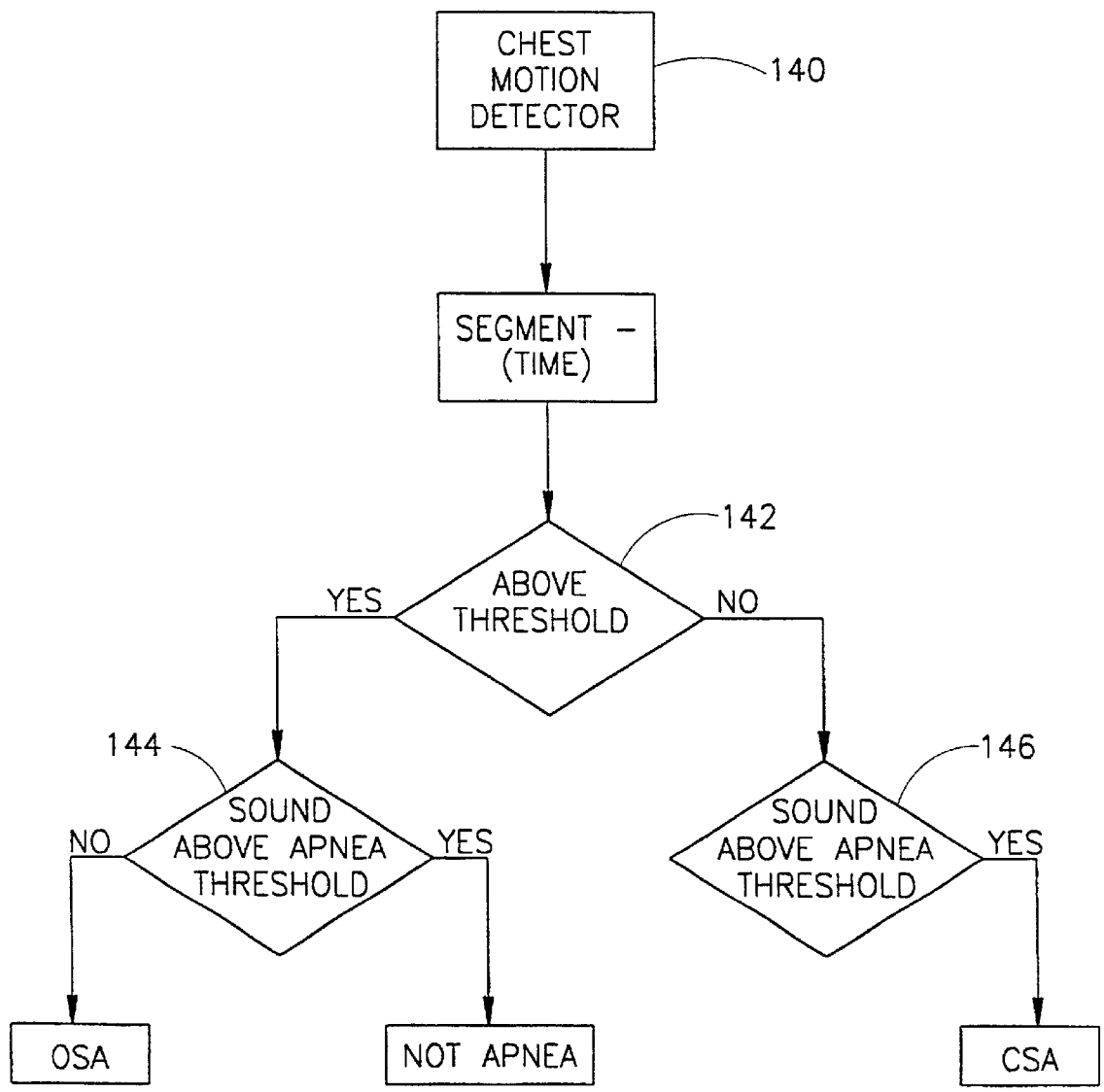
FIG. 1B is a simplified block diagram of a method of differentiating between OSA and CSA, in accordance with a preferred embodiment of the invention.

This is illustrated with the help of FIG. 1B in which an output of a chest motion detector of any suitable type, such as a belt type or other type, known in the art, are used. This output is segmented in time so as to provide an indication of breathing activity.

A threshold is determined for chest motion. In a preferred embodiment of the invention, the chest motion is averaged over a period of normal breathing, preferably, during sleep. The apnea chest motion threshold is then set at some low value of this average, typically 10%. However, as with the breath sounds average, a lower level may be used.

If the motion is above the threshold (step 142) then, if the breath sound, determined at 128 is also above the apnea threshold for breath sound, apnea is not present. On the other hand, if the chest motion is above the threshold and the tracheal sound is below the threshold, this indicates an obstruction and OSA. It should be noted that chest motion of up to 30 percent of normal is not uncommon in this condition.

On the other hand if both chest motion and tracheal sound are below their thresholds, then CSA is indicated.

FIGS. 1A and 1B have been presented in a mixed functional/structural form. However, in a preferred embodiment of the invention, all of the processing on digital signals is carried out in a computer. As used herein, the term circuitry means either dedicated hardware, a computer programmed to carry out a task or a combination of the two.

Figure 2:
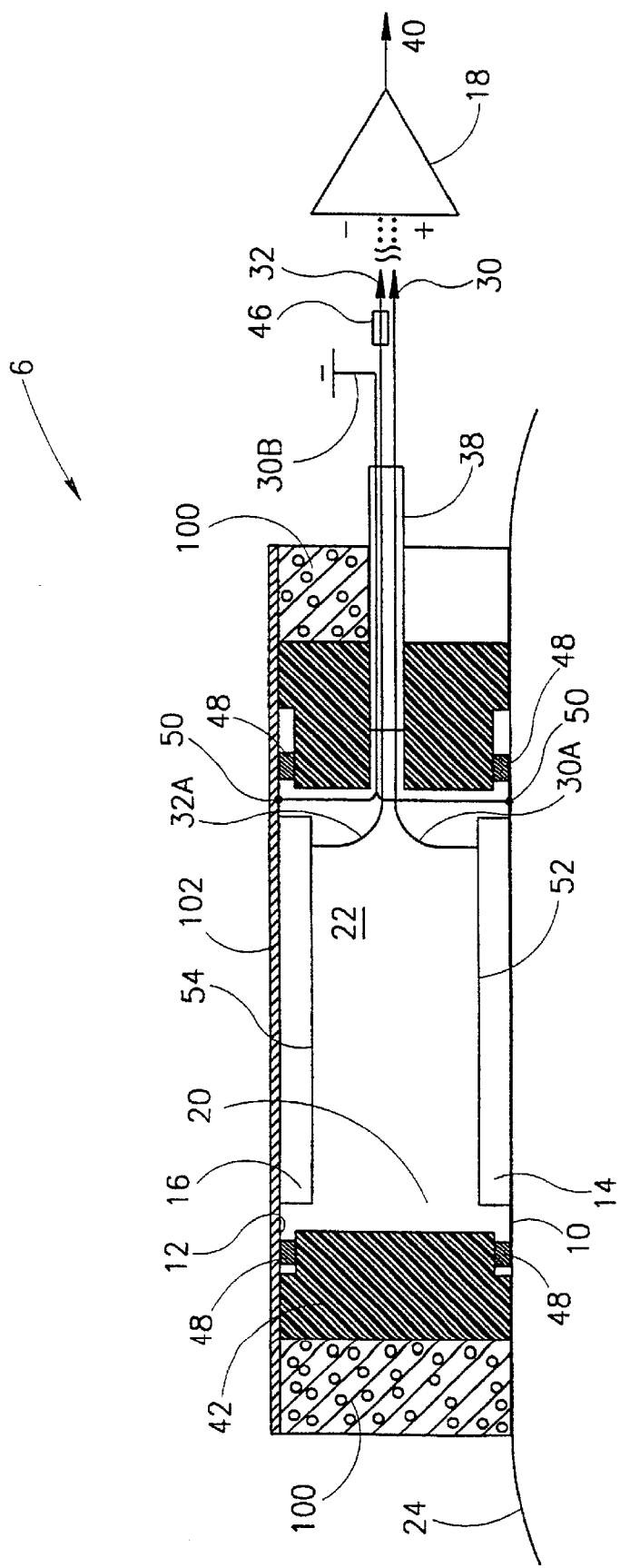
FIG. 2 is a cross-sectional drawing of a breath sounds sensor in accordance with a preferred embodiment of the invention.

FIG. 2 shows a cross-sectional view of a breath sounds sensor in accordance with a preferred embodiment of the invention. This breath sounds sensor is the subject of PCT application PCT/IL98/00172 titled "Sensor for Body Sounds," the disclosure of which is incorporated herein by reference, filed on Apr. 8, 1998 in the Israel receiving office. The sensor of FIG. 2 includes two membranes 10 and 12 which are coupled by an intervening medium 22. Two transducers 14 and 16 are mounted on the membranes and produce signals in response to the vibrations of the membranes. When the output of transducer 16 is subtracted from that of transducer 14 ambient sound is canceled to a substantial extent. This difference signal is preferably utilized for the breath sound of reference 100 of FIG. 1 of the present application. In addition, the output of transducer 16 may be used as the ambient sound sensor of reference 110 of FIG. 1. The reader is referred to this PCT application for more details of the construction and operation of the sensor.

It should be understood that while the sensor of FIG. 2 is preferred, any breath sound sensor, as known in the art may be used in the practice of the invention, with generally separate breath sound and ambient sensors.

The present invention has been explained in the context of preferred embodiments thereof. However, many of the details which have been presented are part of the best mode of carrying out the invention and need not be present in various other embodiments of the invention. Furthermore, persons of skill in the art will appreciate that will appreciate that many variations on the best mode of the invention, as the invention is defined by the following claims are possible.

As used herein the terms "comprise", "include" and their conjugates mean "including but not limited to".

What is claimed is:

1. A method of differentiating between OSA and CSA comprising:
   determining if chest motion above a chest motion threshold is present;
   determining if tracheal breath sound above a breath sounds threshold are present;
   classifying a state as OSA if the chest motion is above the threshold and the sounds are below the threshold; and
   classifying a state as CSA if both the chest motion and sounds are below their respective thresholds.

2. A method according to claim 1 wherein said determining is performed on time segments of the chest motion and breath sounds.

3. A method according to claim 1 wherein the chest motion threshold is determined based on a percentage of motion during normal breathing.

4. A method according to claim 3 wherein the chest motion threshold is between about 5% and about 10%.

5. A method according to claim 3 wherein the chest motion threshold is about 10% of a normal breathing chest motion.

6. A method according to claim 3 wherein the normal breathing is normal breathing during sleep.

7. A method according to claim 1 wherein determining whether tracheal breath sounds are present includes:
   producing a spectrum of the breath sound signal;
   summing averaging the spectrum over a given frequency range to produce a breath sounds power signal.

8. A method according to claim 7 and including producing a separate breath sound spectrum for each of a plurality of given time periods.

9. A method according to claim 1 and including:
   producing a breath sounds power signal representative of the breath sounds power in a plurality of given time periods; and
   integration circuitry which receives the breath sounds power signal; and
   producing a running time average or integral of the breath sounds power signal over a second given time period.

10. Breath sounds apparatus for classifying a breathing state comprising:
    a chest motion sensor and produces a chest motion signal;
    a tracheal breath sound sensor that produces a breath sound signal;
    computing circuitry that receives the breath sound signal and the chest motion signal and determines if chest motion above a chest motion threshold is present and if tracheal breath sound above a breath sounds threshold is present and classifies a breathing state as OSA if the chest motion is above the threshold and the sounds are below the threshold and classifies a breathing state as CSA if both the chest motion and sounds are below their respective thresholds.

11. Breath sounds apparatus according to claim 10 wherein the computing circuitry includes:
    spectrum producing circuitry which receives the breath sound signal and produces a spectrum of the breath sound signal; and
    averaging circuitry which receives the spectrum and sums or averages the spectrum over a given frequency range to produce a breath sounds power signal, wherein the breath sounds power signal is used in the determination of whether the breath sounds are above their threshold.

12. Apparatus according to claim 11 wherein the given frequency range has a lower frequency limit of at least 200 Hz.

13. Apparatus according to claim 11 wherein the given frequency range has a lower frequency limit of at least 250 Hz.

14. Apparatus according to claim 11 wherein the given frequency range has a lower frequency limit of at least 300 Hz.

15. Apparatus according to claim 11 wherein the given frequency range has a lower frequency limit of at least 350 Hz.

16. Apparatus according to claim 11 wherein the given frequency range has a lower frequency limit of at least 400 Hz.

17. Apparatus according to claim 12 wherein the given frequency range has an upper frequency limit of 1200 Hz or less.

18. Apparatus according to claim 12 wherein the given frequency range has an upper frequency limit of 1300 Hz or less.

19. Apparatus according to claim 12 wherein the given frequency range has an upper frequency limit of 1400 Hz or less.

20. Apparatus according to claim 12 wherein the given frequency range has an upper frequency limit of 1500 Hz or less.

21. Apparatus according to claim 12 wherein the given frequency range has an upper frequency limit of 1800 Hz or less.

22. Apparatus according to claim 12 wherein the given frequency range has an upper frequency limit of 2000 Hz or less.

23. Apparatus according to claim 11 wherein the given frequency range is at least 800 Hz.

24. Apparatus according to claim 11, wherein the spectrum producing circuitry produces a separate breath sound spectrum for each of a plurality of given time periods.

25. Apparatus according to claim 24 wherein the given time period is greater than 20 msec.

26. Apparatus according to claim 24 wherein the given time period is greater than 50 msec.

27. Apparatus according to claim 24 wherein the given time period is greater than 75 msec.

28. Apparatus according to claim 24 wherein the given time period is shorter than 200 msec.

29. Apparatus according to claim 24 wherein the given time period is shorter than 150 msec.

30. Apparatus according to claim 24 wherein the given time period is shorter than 100 msec.

31. Apparatus according to claim 24 wherein the given time period is shorter than 75 msec.

32. Apparatus according to claim 24 wherein the given time period is shorter than 50 msec.

33. Apparatus according to claim 11 and including integration circuitry which receives the breath sounds power signal and produces a running time average or integral of the breath sounds power signal over a second given time period.

34. Apparatus according to claim 33 wherein the second given time period is at least 5 seconds.

35. Apparatus according to claim 33 wherein the second given time period is about 6 seconds.

36. Apparatus according to claim 33 wherein the second given time period is about 8 seconds.

37. Apparatus according to claim 33 wherein the second given time period is about 10 seconds.

38. Apparatus according to claim 33 wherein the second given time period is between about 10–15 seconds.

39. Apparatus according to claim 33 wherein the second given time period is between about 15–20 seconds.

40. Apparatus according to claim 11 and including comparison circuitry which receives the averaged or integrated breath sounds power signal and produces an apnea indication if the averaged breath sounds power signal is below a given apnea threshold.

41. Apparatus according to claim 40 wherein the given apnea threshold is based on a breath sounds power signal acquired during normal breathing.

42. Apparatus according to claim 41 wherein the given apnea threshold is about 10% of the a breath sounds power signal acquired during normal breathing.

43. Apparatus according to claim 42 wherein the given apnea threshold is between 5% and 10% of the a breath sounds power signal acquired during normal breathing.

44. Apparatus according to claim 11 and including comparison circuitry which receives the averaged or integrated breath sounds power signal and produces an hypopnea indication if the averaged breath sounds power signal is below a given hypopnea threshold.

45. Apparatus according to claim 44 wherein the given hypopnea threshold is based on a breath sounds power signal acquired during normal breathing.

46. Apparatus according to claim 45 wherein the given hypopnea threshold is about 25% of the a breath sounds power signal acquired during normal breathing.

47. Apparatus according to claim 45 wherein the given apnea threshold is between 20% and 30% of the a breath sounds power signal acquired during normal breathing.

48. Apparatus according to claim 10 and including:

an ambient sound sensor which produces an ambient sound signal responsive to ambient sounds;

spectrum producing circuitry which receives the ambient sound signal and produces a spectrum of the ambient sound signal;

comparison circuitry which compares the spectrum of the ambient sound spectrum with a threshold spectrum and produces a signal for those frequencies for which the spectrum is greater than the threshold; and spectrum conditioning circuitry which conditions the breath sound spectrum by replacing the value of the breaths sounds spectrum by a different value for those frequencies for which the ambient sound spectrum exceeds the threshold.

49. Apparatus according to claim 48 wherein the threshold is based on an ambient sounds spectrum produced in the absence of substantial ambient sound.

50. Apparatus according to claim 49 wherein the threshold at a given frequency is determined, from a plurality of spectra of the ambient sound, as the average of value of the spectrum at the given frequency plus a factor times the standard deviation of the values of the spectrum.

51. Apparatus according to claim 50 wherein the factor is more than 3.

52. Apparatus according to claim 51 wherein the factor is between 4 and 6.

53. Apparatus according to claim 48 wherein the spectrum conditioning circuit replaces the value of the breaths sounds spectrum by a zero for those frequencies for which the ambient sound spectrum exceeds the threshold.

54. Apparatus according to claim 48 wherein the spectrum conditioning circuit replaces the value of the breaths sounds spectrum by a value equal to the average of values for adjacent frequencies, for those frequencies for which the ambient sound spectrum exceeds the threshold.

* * * * *